United States Patent [19]

Evans

[11] Patent Number: 5,022,273

[45] Date of Patent: Jun. 11, 1991

[54] APPARATUS AND METHOD FOR TESTING THE BENDING STRENGTH OF NEEDLES

[75] Inventor: Alfred G. Evans, Torrington, Conn.

[73] Assignee: United States Surgical Corporation, Norwalk, Conn.

[21] Appl. No.: 535,849

[22] Filed: Jun. 11, 1990

[51] Int. Cl.⁵ ............................................. G01N 3/20
[52] U.S. Cl. ................................................... 73/849
[58] Field of Search ................. 73/849, 851, 850, 161

[56] References Cited

U.S. PATENT DOCUMENTS

| 4,160,325 | 7/1979 | De Nicola | 33/148 D |
| 4,194,402 | 3/1980 | De Nicola | 73/859 |
| 4,721,000 | 1/1988 | Scanlon | 73/833 |

FOREIGN PATENT DOCUMENTS

| 738878 | 12/1932 | France | 73/851 |
| 50136 | 3/1969 | German Democratic Rep. | 73/849 |
| 1456111 | 2/1989 | U.S.S.R. | |

*Primary Examiner*—Jerry W. Myracle
*Attorney, Agent, or Firm*—Thomas R. Bremer; Peter G. Dilworth; Rocco S. Barrese

[57] ABSTRACT

An apparatus and method is disclosed for determining the bending strength of curved surgical needles. The apparatus includes a means to releasably grip the butt end portion of the needle connected to a rotatable flywheel. A knife edge is positioned in the path of the rotating needle and engaged thereby, while a load cell to which the knife edge is connected, generates signals in dependence upon the bending movements applied to the needle. Such signals are transmitted to appropriate monitoring and recording instrumentation. The rotation of the needle with respect to a center of rotation and with respect to the knife edge are maintained to within precise limitations.

34 Claims, 7 Drawing Sheets

APPARATUS AND METHOD FOR TESTING THE BENDING STRENGTH OF NEEDLES

BACKGROUND OF THE INVENTION

1. Field Of The Invention

The present invention relates to testing the bending strength of needles. In particular, the invention relates to an apparatus and method to determine the bending strength and ductility of a curved surgical needle by precision application of known bending moments and by monitoring the resultant forces and moments generated.

2. Description of Related Art

Various methods and apparatus for measuring the bending strength of surgical needles are known. Generally, a needle to be tested is fixed at one end in a device for measuring stress and strain. A bending force is then applied to the needle. The amount of force necessary to achieve bending of the needle is then measured. In particular, with curved surgical needles, the accurate and consistent application of a bending moment has proven to be difficult, particularly due to the curvature of the needle. For example, in order to apply a bending moment which is consistent over a period of time and rotational span, the force and the direction of the moment arm must be maintained with consistency and extreme precision. Furthermore, this precision must be maintained throughout the bending action of the needle.

There are known methods to measure stress, strain and other material strength characteristics of a sample of material These methods include manual manipulation of the material to subjectively feel the strength. This method is not uniform and does not indicate force requirements for deformation of the material. Extensometers measure minute deformations of a test specimen caused by tension, compression, bending or twisting.

It is significant to obtain both strain and deflection readings simultaneously because both types of strain, e.g., axial strain and bending deflection will occur even when stress is applied in only one direction. Therefore, in order to fully evaluate a specimen, both stress measurements are needed. Some techniques for determining axial and bending moment values may interfere with each other and prevent simultaneous accurate measurement.

In dynamic testing apparatus, a specimen of material is subject to a variety of test loads. These may include tension, compression and torsion. A major problem with many apparatus is that the devices which secure or clamp the test specimen have created unwanted, nonuniform stresses and strains on the specimen because of the manner in which the specimen is secured. For example, gripping of the ends of a specimen will introduce compression tension or shear forces, resulting in errors in the test results. If a sample is not perfectly aligned with the two gripping devices, non uniform loading of the sample will result.

Figure 1:
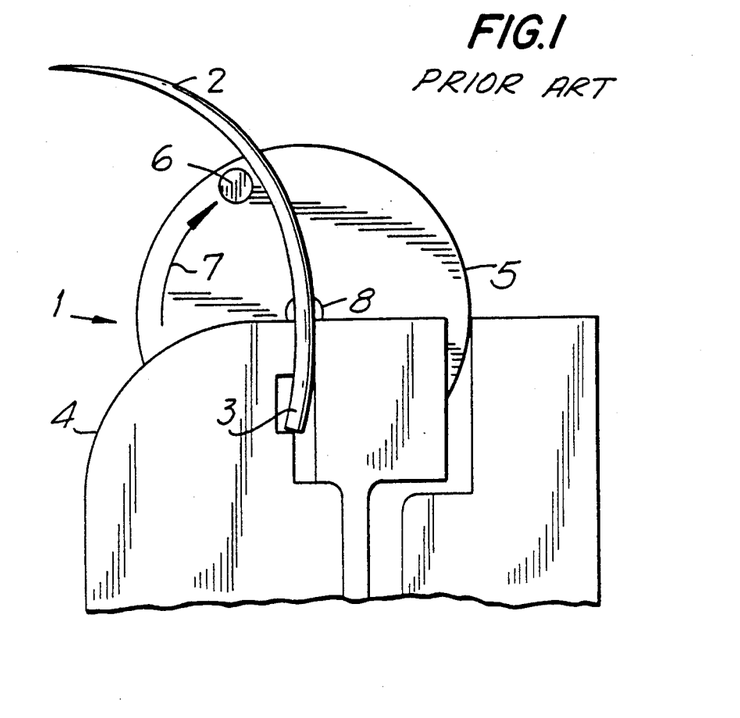
FIG. 1 is a diagrammatic view of a known apparatus for measuring the bending strength of curved needles.

Difficulties encountered in prior attempts to test the bending strength of curved needles are shown in FIG. 1 which illustrates a known device 1 for measuring the bending strength of a curved surgical needle 2. The barrel end 3 of the needle is placed in the needle gripping fixture 4 of the instrument. Rotary actuator 5 has a peg 6 for contacting the needle 2. To measure the bend strength of needle 2, actuator 5 is rotated in the direction of arrow 7 about central axis 8. Peg 6 contacts the concave side of the needle and is supplied with sufficient force to bend the needle. The applied force is measured by appropriate force sensing instrumentation.

Bending stresses are developed in the needle around the area contacted by the gripping fixture. However, it can be seen that the point of application of the force by peg 6 will change relative to the needle, causing inaccuracies in the resultant measured stresses. These stresses are non-uniform in magnitude and direction, and such non-uniformity introduces a source of error in the measurement of the bending strength of the needle.

I have invented an apparatus and method for securing and testing needles for determining the bending strength and ductility in a manner which provides improved accuracy and precision, with resultant uniform and accurate measurements.

SUMMARY OF THE INVENTION

An apparatus is disclosed for determining the bending strength of a needle, which comprises means to releasably grip the needle at one end portion, means to rotate the needle gripping means and the needle, means positioned within the rotatable path of the needle so as to engage the needle at a predetermined location, and means to provide signal means in dependence upon forces applied to the needle engaging means by the needle.

Preferably, the apparatus for determining the bending strength of a needle comprises means to releasably grip the needle at one end portion, means to rotate the needle gripping means—and the needle—such that a predetermined surface portion of the needle is equidistant from the point of rotation through the range of rotation, knife edge means positioned with respect to the needle so as to engage the needle within the range defined by the predetermined surface portion, and means connected to the knife edge means and adapted to receive forces generated by the needle thereagainst and to provide signal means in dependence on the generated forces.

The signal providing means is preferably a load cell and the means to releasably grip the needle is preferably a clamp. The clamp is preferably attached to a rotatable member—in the form of a slow rotation flywheel—and the rotatable member is adapted to rotate about a fixed center at all time. Motor means, preferably a stepper motor connected to transmission means, is provided to rotate the rotatable member and the needle.

The needle clamp is dimensioned and configured to grip the needle such that when the clamp is rotated, the distance between the center of rotation of the needle and the point of contact with the knife edge means is substantially constant. Further, the clamp is adapted to grip the butt end portion of the needle and preferably the needle is a curved surgical needle which has arcuate —i.e. circular—surface portions.

Means is provided to monitor the signal provided by the load cell, and means is provided to record the signal provided by the load cell. Either monitoring or recordation, or both, may be utilized simultaneously. Further, means is provided to adjust the horizontal portion of the clamp and the needle with respect to the knife edge means and means is provided to adjust the vertical position of the clamp and the needle with respect to the knife edge means such that rotation of the clamp and the needle within a predetermined range will cause the needle to engage the knife edge means against a predetermined surface portion of the needle.

The bending strength of the needle is determined from the signal provided by the load cell. Further, the first knife edge means is preferably oriented vertically and a second knife edge means is positioned adjacent the first knife edge means and oriented horizontally so as to engage the needle when it is rotated in a direction opposite the first rotational direction. The second knife edge means is preferably connected to the load cell and adapted to generate a signal in dependence upon force transmitted to the second knife edge means when the needle engages the second knife edge means during rotation in the second rotational direction. Means is provided to determine the ductility of the needle utilizing the force data provided by the signal means in the first and second rotational directions of the needle.

A method is disclosed for determining the bending strength of a needle which comprises releasably gripping the needle at one end portion, rotating the needle in a first direction about an axis transverse to the butt end of the needle such that a predetermined surface portion of the needle is equidistant from the point of rotation of the needle throughout the range of rotation of the needle, engaging the needle in the path of rotation thereof within a predetermined surface portion defined by the needle, and providing signal means in dependence on force transmitted by the needle to the needle engagement means. The needle engagement means preferably defines a knife edge positioned in the path of the needle for engagement therewith. The knife edge means is preferably connected to means capable of providing signal means in dependence on force transmitted by the needle to the knife edge means. The means to generate signal means in dependence on force transmitted by the needle is preferably a load cell. The method further comprises transmitting the signal means to monitor means and/or transmitting the signal means to recording means.

The method also comprises determining the bending strength and yield point of the needle based upon the signal means provided and rotating the needle in a second direction opposite the first direction after completion of the first rotational motion. The surface portion of the needle opposite the first surface of engagement is engaged by second knife edge means such that the needle transmits force to the second knife edge means when the needle is rotated back to its original orientation. The force provided by the needle against the second knife edge means is preferably transmitted to signal generating means to produce signal means in dependence on the force transmitted to the second knife edge means. The method further comprises alternately repeating the rotation of the needle in the first and second directions a predetermined number of cycles sufficient to break the needle. Thereby, the bending strength and yield point of the needle may be determined. Further, the ductility of the needle can be determined by subjecting the needle to sufficient reversing cycles to induce breakage.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

The bending strength of a needle is defined by the amount of bending torque required to cause permanent bending deformation of the needle and is evaluated by the analysis of a bending force-rotation curve. This test is performed by the testing fixture and method of the present invention, preferably in combination with an Instron Universal Testing Apparatus, e.g. Instron Model 1123, available from the Instron Corp. of Canton, Mass. 02021. Of particular interest is the measurement of the bending yield load of a surgical needle at a perpendicular distance of one centimeter from the axis of rotation of the applied bending force. The yield load is defined as the amount of force required for the onset of plastic deformation and is the two degree (i.e. 2°) offset determination of a bending force-rotation curve.

The apparatus of the present invention generally includes a rotatable needle mounting fixture. The needle is rotated against a blade member until the needle bends. When the needle engages the blade, the blade receives an applied force. This force is received by force sensing instrumentation, and information relating to the magnitude of the force is transmitted to computational instrumentation for analysis.

Figure 2:
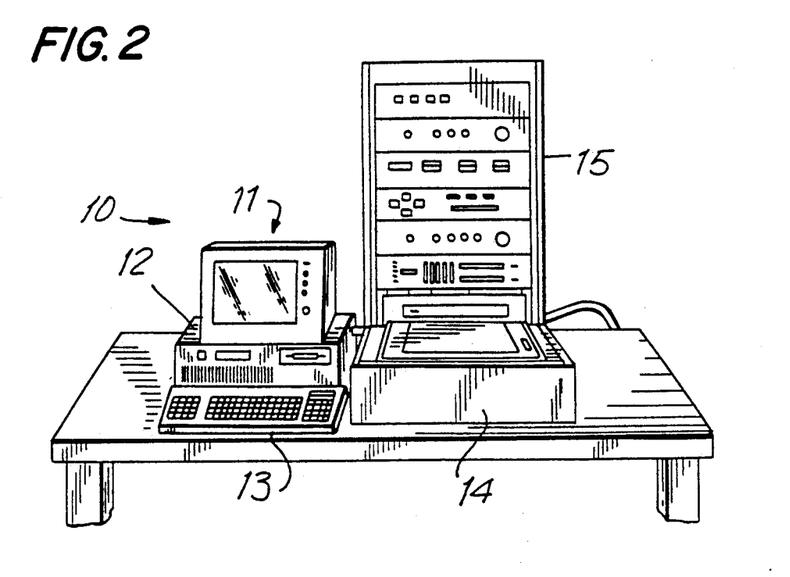
FIG. 2 is an elevational view of the computational instrumentation of the present invention.

FIG. 2 illustrates a computer station having the computational instrumentation 10 of the present invention. The computer station includes a computer 12 with monitor 11, keyboard 13, and (printer/plotter) 14. The computer can be an IBM PC/AT with Instron Series IX Software Version. Control instrumentation 15, such as DAEDAL MC 2000 Controller available from Daedal, Inc., Harrison City, Pa. 15636, receives electrical signals from the sensing instrumentation and converts these signals to stress and strain data. Control instrumentation 15 further provides a means for controlling the magnitude and rate of application of bending force to the sample needle.

Figure 3:
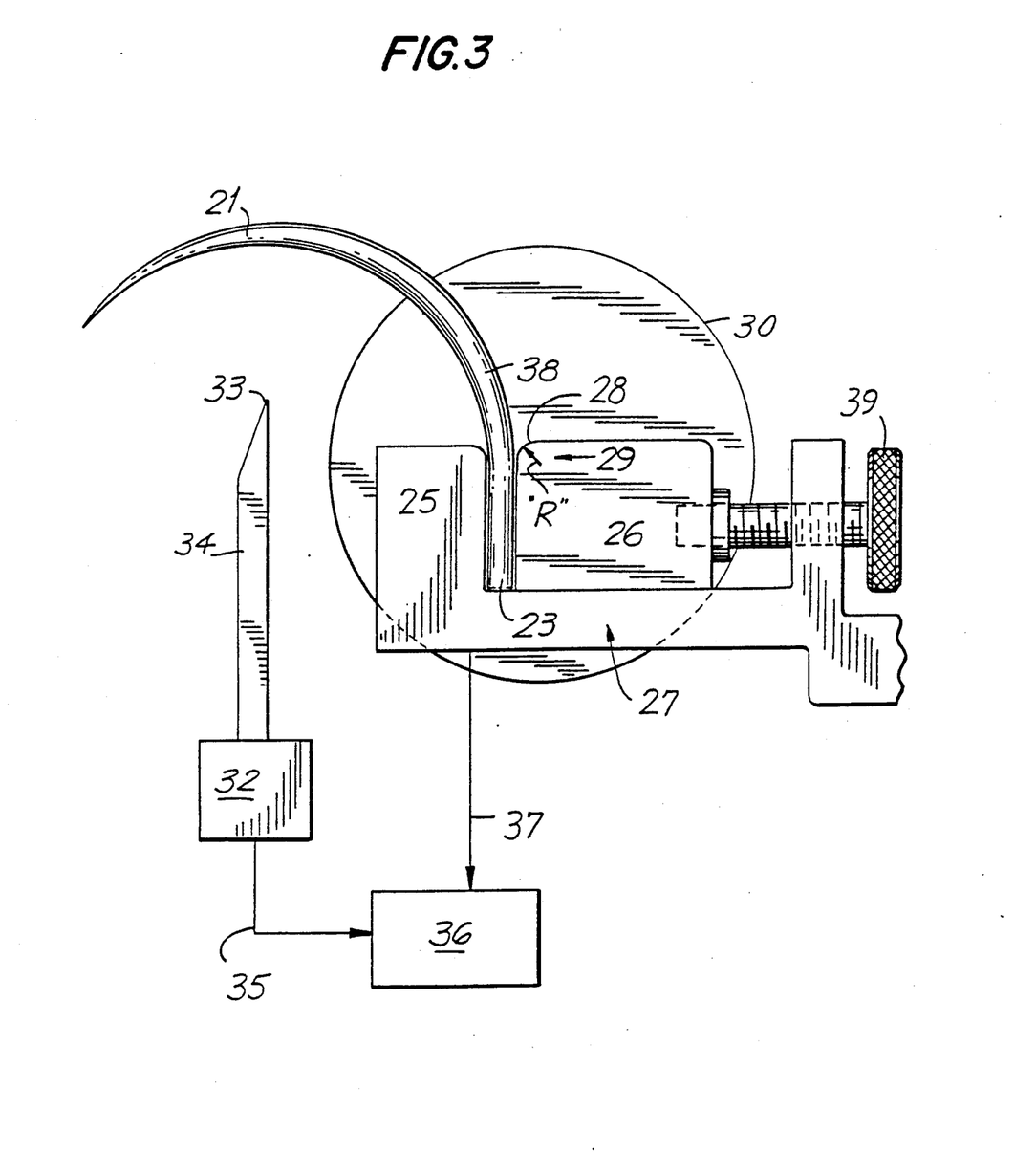
FIGS. 3, 3A, and 4 are enlarged diagrammatic views of the present invention illustrating the needle mounting fixture in preliminary, starting, and rotated positions, respectively.
Figure 3A:
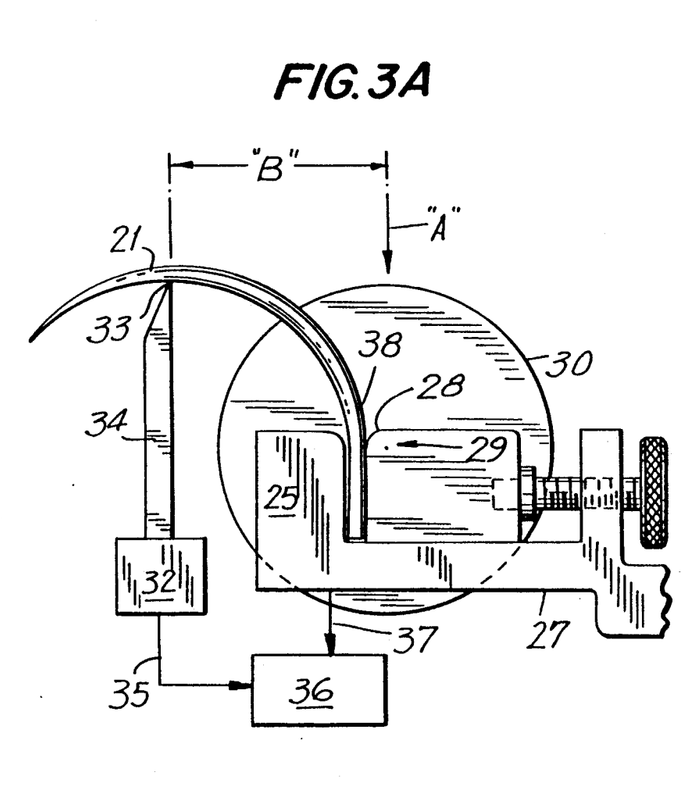
Figure 4:
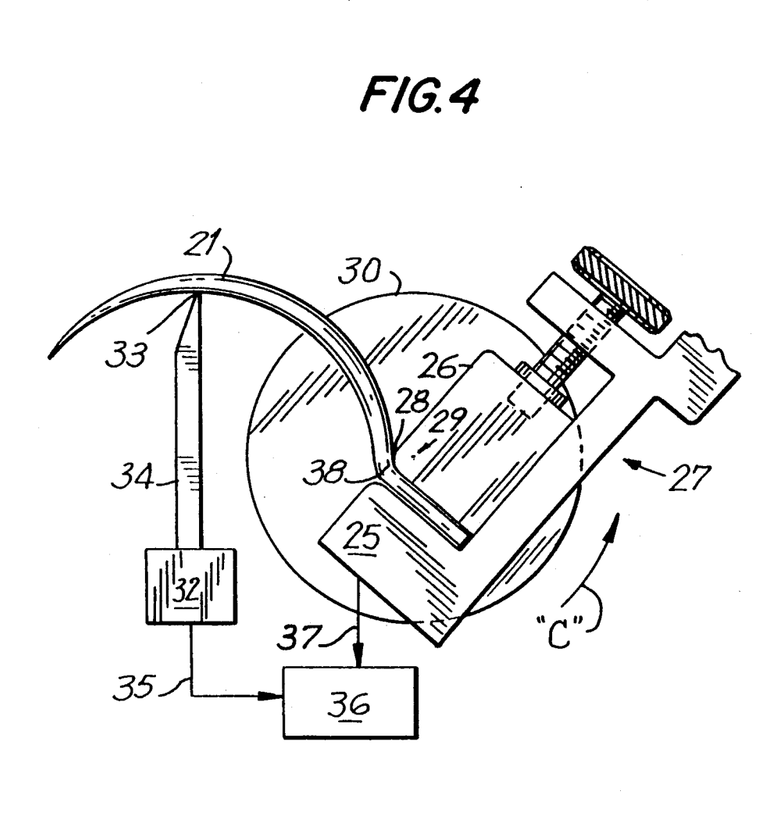

FIGS. 3, 3A, and 4 illustrate diagrammatically the needle testing method and apparatus of the present invention. Referring particularly to FIG. 3, the surgical needle to be tested for bending strength, i.e. surgical needle 21 is positioned in the needle mounting fixture 27 such that the barrel end 23 of the needle is located between jaws 25 and 26 of the mounting fixture 27. Jaw 25 is fixedly positioned relative to the mounting fixture 27. Jaw 26 is manually adjustable by means of adjustment screw 39 which moves jaw 26 laterally toward or away from jaw 25 so that needle 21 can be clamped securely between the jaws. Jaw 26 has a rounded or curved edge 28 adjacent the needle 21. The curved edge 28 has a center of curvature located at point 29 and preferably a radius of curvature "R" of about 0.025 inches. The needle mounting fixture 27 is mounted to a rotary actuator 30 having an axis of rotation coinciding with center point 29. FIG. 3 illustrates the apparatus in a preliminary position prior to testing the needle.

Referring now to FIG. 3A, when the needle 21 has been securely mounted, the mounting fixture 27 and actuator 30 are moved vertically downward from the position in FIG. 3 in the direction shown by arrow A until the needle 21 just contacts the knife edge 33 of blade 34 at a point preferably about 1 centimeter away from the axis of rotation 29 of needle mounting fixture 27 as shown by dimension "B". Distances other than 1 centimeter can also be used for measurement depending upon the size of the needle being tested.

Referring now to FIG. 4, when actuator 30 is rotated in the direction shown by arrow "C" in FIG. 4, a bending force is applied to the needle. The actuator is provided with force sufficient to continue the rotation, preferably to complete approximately a 90 degree rotation. Thus, needle 21 will bend at area 38 in a direction opposite to that of the actuator rotation as shown in FIG. 4. The actuator 30—or flywheel—can be pre-set to rotate at a predetermined angular velocity from about one degree per second to about four degrees per second. Preferably, the velocity of rotation should be set at about two degrees per second.

Load cell 32 shown schematically in the Figs., receives a downward force from the needle and converts this force into an electrical signal which carries information relating to the magnitude of the force via signal transmission line 35 to signal reception means 36, which is located in control instrumentation 15, shown in FIG. 2. A preferred load cell is the Instron Brand A31-17 Load Cell which is available from Instron Corp., Canton, Mass. 02021 in 1000 gram and 5000 gram load capacities. Alternatively an Instron Model 1123 load cell may be employed having capacity of up to about 50 lbs. Information relating to the positioning, speed of rotation, and force of rotary actuator 30 is carried by a signal via line 37 to signal reception means 36. Various types of instrumentation suitable for signal reception means 36 are known and available to those skilled in the art.

In prior known devices the edges of the mounting jaws are relatively sharp and tend to cut into the needle in area 38 as force is applied. This results in an unwanted concentration of stress which interferes with accurate measurement of the overall bending strength.

In contrast to the prior known apparatus, the apparatus of the present invention provides a curved bending surface 28 to distribute the bending forces generated at area 38 in the needle. Furthermore, location of the axis of rotation of actuator 30 at point 29, which is also the center of curvature of surface 28, prevents surface 28 from cutting into the needle. Rather, area 38 of the needle wraps around curved surface 28 as the needle is bent. This provides greater consistency of the resultant data. In the present invention, drive motor 51 is preferably a stepper motor which is coupled by transmission system 53 to provide precise control over the rotational motion of actuator 30.

Figure 5:
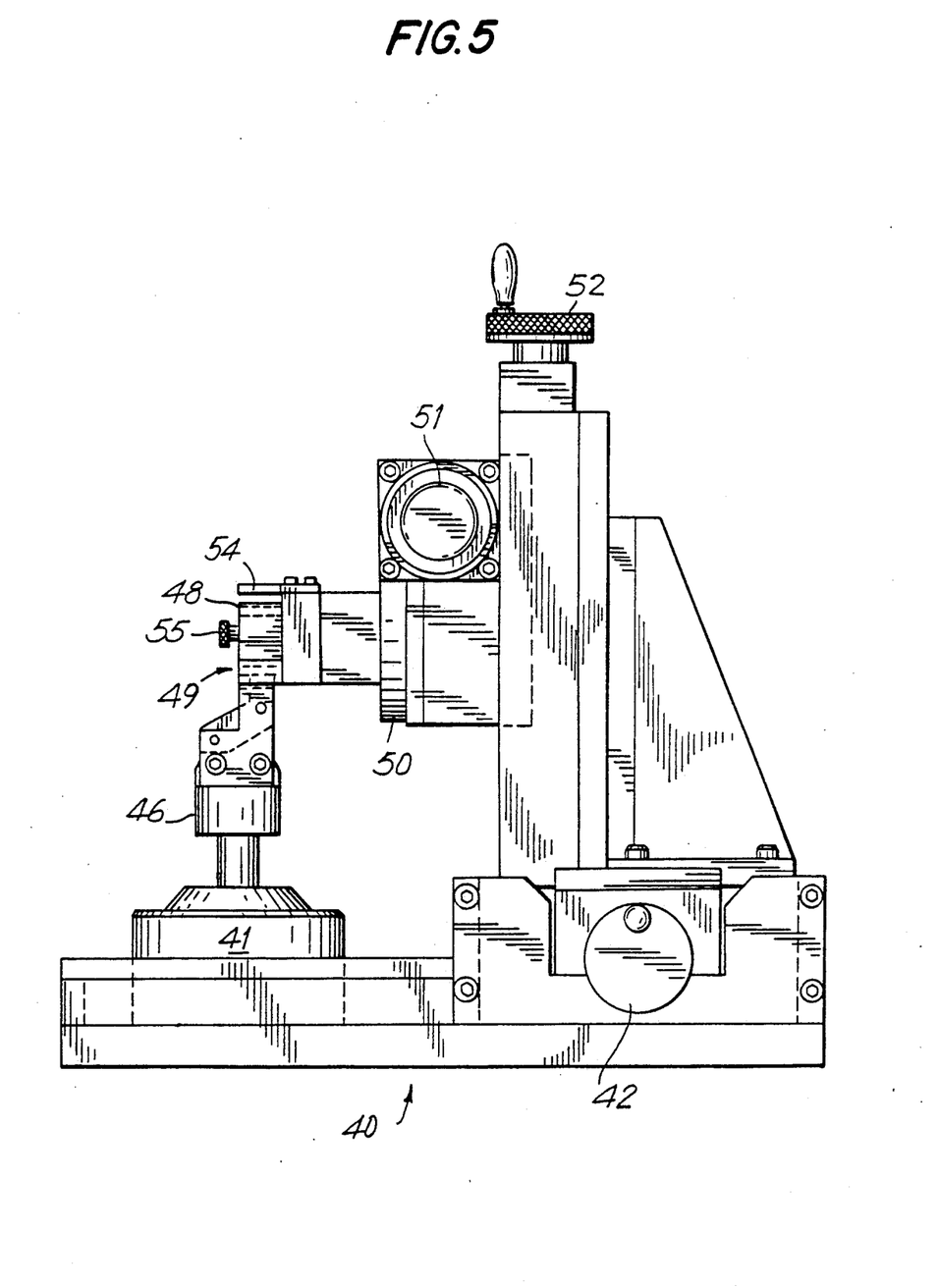
FIG. 5 is a side elevational view of the needle bending test apparatus of the present invention.
Figure 6:
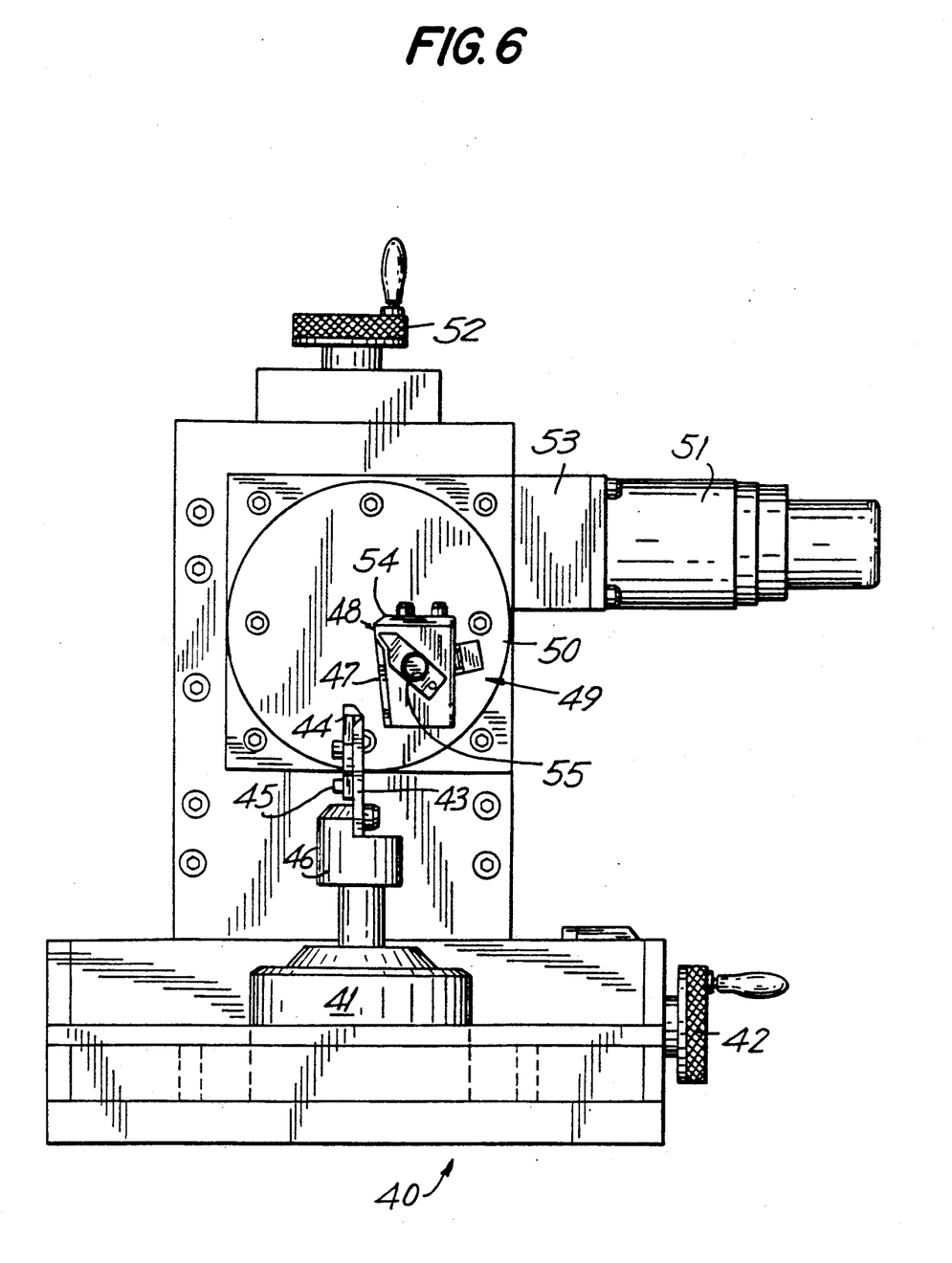
FIG. 6 is a front elevational view of the needle bending test apparatus of the present invention.
Figure 7:
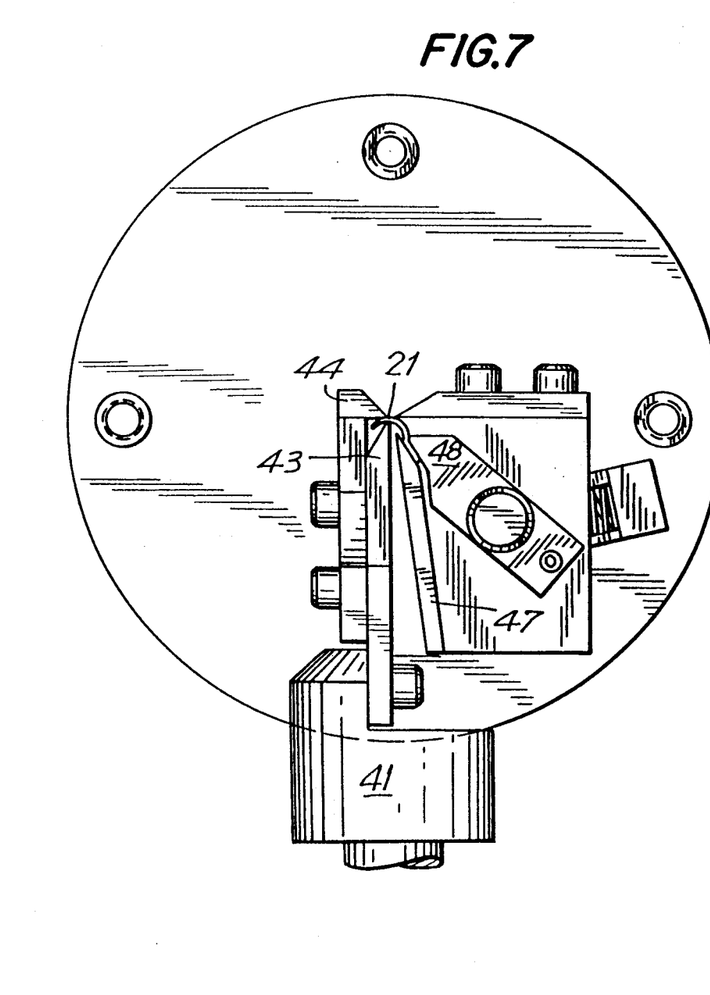
FIG. 7 is a front elevational view of an alternative embodiment of the present invention utilized to determine needle ductility.
Figure 8:
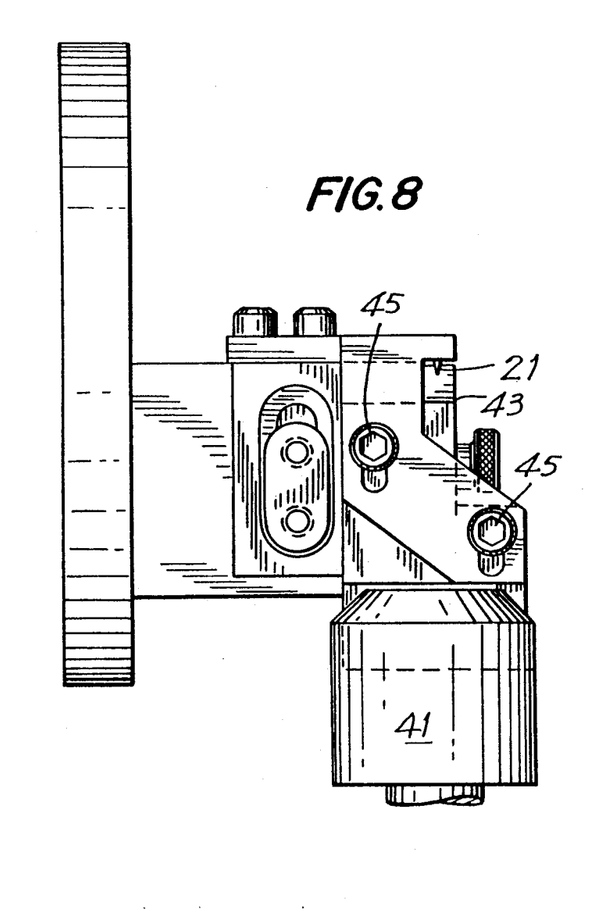
FIG. 8 is a side elevational view of the apparatus shown in FIG. 7.
Figure 9:
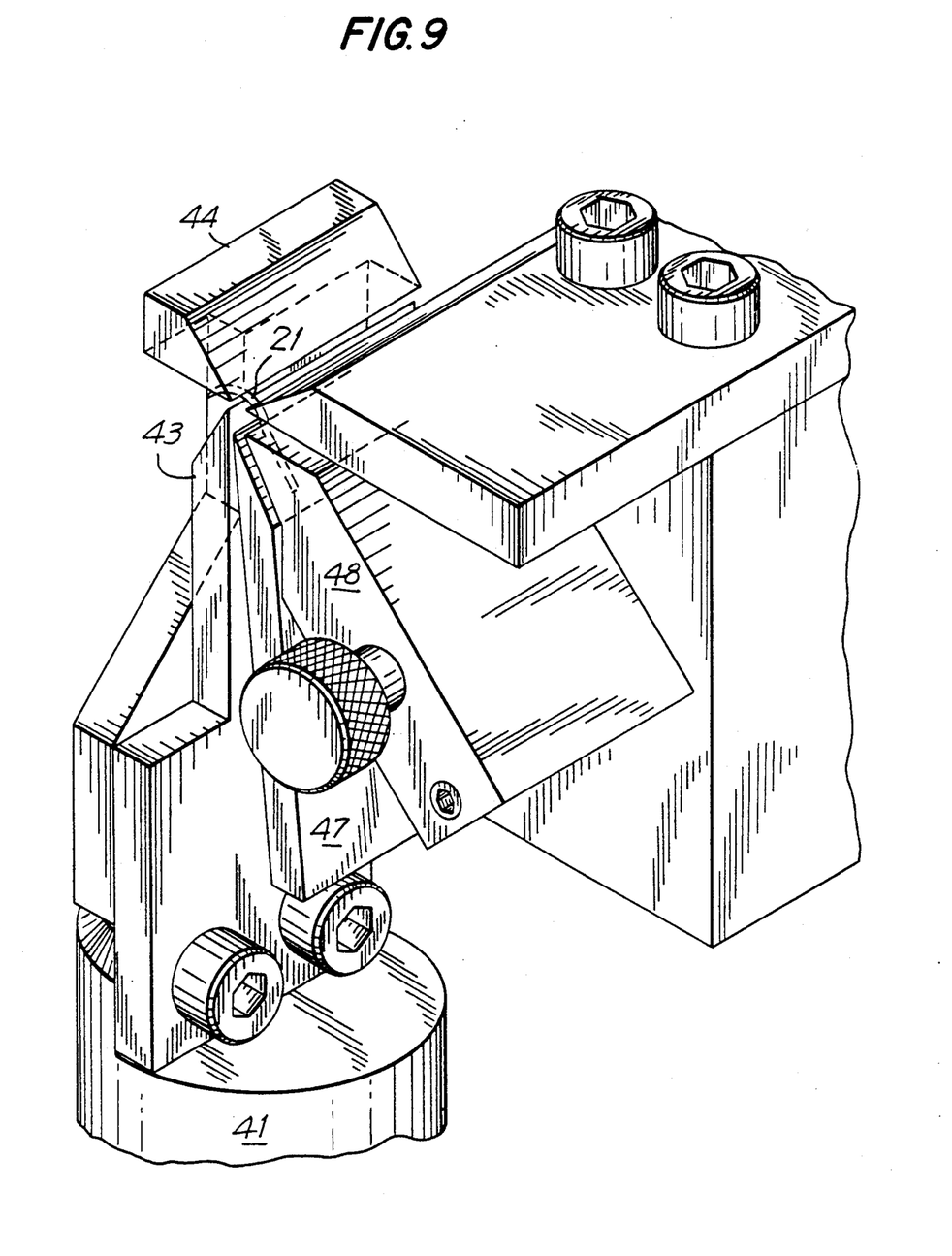
FIG. 9 is a perspective view of the needle mounting fixture of the apparatus shown in FIG. 7, in a needle bending position.

Referring now to FIGS. 5, 6, 7, 8, and 9 there is illustrated an alternative embodiment 40 of the present invention. Referring initially to FIGS. 5 and 6, alternative embodiment 40 includes a needle mounting fixture 49 having first and second jaws 47 and 48, for mounting a surgical needle as illustrated in FIGS. 7, 8, and 9, and a top plate 54. The first jaw 47 is fixedly positioned relative to the mounting fixture 49, whereas the second jaw 48 is adjustable by means of screw 55 which, when loosened, allows the second jaw 48 to pivot. When screw 55 is tightened the second jaw 48 is locked into a fixed position relative to the first jaw 47. Needle mounting fixture 49 is mounted to rotary actuator 50, which is rotated by stepper motor 51. Vertical positioning of the mounting fixture 49 is accomplished by rotating crank handle 52.

Vertical blade 43 is mounted on blade mounting fixture 46, which is mounted to a load cell 41 as in the previously described embodiment. Horizonal blade 44 is mounted to the lower blade 43 and can be vertically adjusted by means of screws 45 such that the portion of a surgical needle inserted between the edges of the upper and lower blades, will not be moved when the mounting fixture 46 is rotated. Handcrank 42 and associated drive mechanism (not shown) allows precise manual adjustment of the horizontal position of the load cell 41, blade mounting fixture 46, and blades 43 and 44.

Referring now to FIGS. 7 and 8, it can be seen that horizontal blade 44 and vertical blade 43 are positioned to engage needle 21 when the needle is rotated. When the needle 21 is rotated counterclockwise it engages the upper knife edge of knife 43, thus providing downward force on knife 43 which is transmitted to load cell 41. When the needle is rotated back to its original position (i.e., clockwise) the upper surface of the needle engages knife edge of horizontal knife 44 and provides an upward force to knife 44 and to load cell 41. The rotation of the needle may be alternated respectively, clockwise and counterclockwise until the needle fails in bending, while continuously recording the downward and upward force transmitted to the load cell 41. This recording may then be utilized to determine the ductility of the needle for processing the recorded data in a known manner.

It will be readily appreciated that the present invention represents a significant advantage over the prior art devices, particularly in that the binding moments—or torque—applied to the needle is precise and accurate throughout the range of the rotation. While the invention is particularly advantageous in use with curved surgical needles, it will be readily appreciated that needles of all configurations may be tested with the same degree of accuracy. In the case of curved surgical needles, the needles are generally configured as an arc of a circle having a predetermined radius. Accordingly, in such instances the radius of the needle must be considered in the dimensioning and spacing of the knives 34 and 44. In the case of straight needles or other configurations, the accuracy in determining needle bending strength and ductility is also obtainable with minor modifications known to persons skilled in the art.

What is claimed is:

1. Apparatus for determining the bending strength of a needle which comprises:
   a) means to releasably grip the needle at one end portion;
   b) means to rotate the needle gripping means and the needle;
   c) means positioned within the rotatable path of the needle so as to engage the needle at a predetermined location; and d) means to provide signal means in dependence upon forces applied to said needle engaging means by said needle.

2. Apparatus for determining the bending strength of a needle which comprises:
   a) means to releasably grip the needle at one end portion;
   b) means to rotate the needle gripping means such that a predetermined surface portion of the needle is equidistant from the point of rotation through the range of rotation;
   c) knife edge means positioned with respect to the needle so as to engage the needle within the range defined by said predetermined surface portion; and
   d) means connected to said knife edge means and adapted to receive forces generated by said needle thereagainst and to provide signal means in dependence on the generated forces.

3. The apparatus for determining the bending strength of a needle according to claim 2 wherein said signal providing means is a load cell.

4. The apparatus for determining the bending strength of a needle according to claim 3 wherein said means to releasably grip the needle is a clamp.

5. The apparatus for determining the bending strength of a needle according to claim 4 wherein said clamp is attached to a rotatable member.

6. The apparatus for determining the bending strength of a needle according to claim 5 wherein said rotatable member is adapted to rotate about a fixed center at all times.

7. The apparatus for determining the bending strength of a needle according to claim 6 further comprising motor means to rotate said rotatable member and the needle.

8. The apparatus for determining the bending strength of a needle according to claim 7 wherein said motor is a stepper motor connected to said rotatable member by transmission means.

9. The apparatus for determining the bending strength of a needle according to claim 8 wherein the needle clamp is dimensioned and configured to grip the needle such that when said clamp is rotated, the distance between the center of rotation of the needle and the point of contact with said knife edge means is substantially constant.

10. The apparatus for determining the bending strength of a needle according to claim 9 wherein said clamp is adapted to grip the butt end portion of a curved needle.

11. The apparatus for determining the bending strength of a needle according to claim 10 wherein said needle is a curved surgical needle.

12. The apparatus for determining the bending strength of a needle according to claim 11 wherein the clamp portion adapted to grip the butt end of the needle has arcuate surface portions on each side of the needle which permit the needle to bend thereabout.

13. The apparatus for determining the bending strength of a needle according to claim 12 further comprising means to monitor the signal provided by said load cell.

14. The apparatus for determining the bending strength of a needle according to claim 13 further comprising means to record said signal provided by said load cell.

15. The apparatus for determining the bending strength of a needle according to claim 14 further comprising means to adjust the horizontal portion of said clamp and the needle with respect to said knife edge means.

16. The apparatus for determining the bending strength of a needle according to claim 15 further comprising means to adjust the vertical portion of said clamp and the needle with respect to said knife edge means such that rotation of said clamp and the needle will cause the needle to engage said knife edge means against said predetermined surface portion.

17. The apparatus for determining the bending strength of a needle according to claim 16 further comprising means to determine the bending strength of the needle from the signal provided by said load cell.

18. The apparatus for determining the bending strength of a needle according to claim 17 wherein said first knife edge means is oriented vertically and a second knife edge means is positioned adjacent said first knife edge means and oriented horizontally so as to engage the needle when it is rotated in a direction opposite the first rotational direction.

19. The apparatus for determining the bending strength of a needle according to claim 18 wherein said second knife edge means is connected to said load cell and adapted to generate a signal in dependence upon force transmitted to said second knife edge means when the needle engages said second knife edge means during rotation in the second rotational direction.

20. The apparatus for determining the bending strength of a needle according to claim 19 further comprising means to determine the ductility of the needle utilizing the force data provided by said signal means in said first and second rotational directions of the needle.

21. Method for determining the bending strength of a needle which comprises:
   a) releasably gripping the needle at one end portion;
   b) rotating the needle in a first direction about an axis transverse to the butt end of the needle such that a predetermined surface portion of the needle is equidistant from the point of rotation of the needle throughout the rotation of the needle;
   c) engaging the needle in the path of rotation thereof within a predetermined surface portion defined by the needle; and
   d) providing signal means in dependence on force transmitted by the needle to said engagable means.

22. The method for determining the bending strength of a needle according to claim 21 wherein said needle engagement means defines a knife edge positioned in the path of the needle for engagement therewith.

23. The method for determining the bending strength of a needle according to claim 22 wherein said knife edge means is connected to means capable of providing signal means in dependence on force transmitted by the needle to said knife edge means.

24. The method for determining the bending strength of a needle according to claim 23 wherein said means to generate signal means in dependence on force transmitted by the needle is a load cell.

25. The method for determining the bending strength of a needle according to claim 23 further comprising transmitting said signal means to monitor means.

26. The method for determining the bending strength of a needle according to claim 25 further comprising transmitting said signal means to recording means.

27. The method for determining the bending strength of a needle according to claim 26 further comprising determining the bending strength and yield point of the needle based upon said signal means.

28. The method for determining the bending strength of a needle according to claim 27 further comprising rotating the needle in a second direction opposite said first direction after completion of said first rotational motion.

29. The method for determining the bending strength of a needle according to claim 28 further comprising engaging the surface portion of the needle opposite said first surface of engagement by second knife edge means such that the needle transmits force to said second knife edge means.

30. The method for determining the bending strength of a needle according to claim 29 further comprising transmitting the force provided by the needle against said second knife edge means to signal generating means to produce signal means in dependence on the force transmitted to said second knife edge means.

31. The method for determining the bending strength of a needle according to claim 30 further comprising alternately repeating the rotation of the needle in said first and second directions a predetermined number of cycles.

32. The method for determining the bending strength of a needle according to claim 31 further comprising repeating said clockwise rotational cycles sufficient to break the needle.

33. The method for determining the bending strength of a needle according to claim 32 further comprising determining the bending strength and yield point of the needle.

34. The method for determining the bending strength of a needle according to claim 33 further comprising determining the ductility of the needle.

* * * * *